US008318497B2

(12) United States Patent
Szpirer et al.

(10) Patent No.: US 8,318,497 B2
(45) Date of Patent: Nov. 27, 2012

(54) REVERSIBLE, PARALLEL AND MULTITASK CLONING METHOD AND KIT

(75) Inventors: Cédric Szpirer, Fleurus (BE); Michel C. Milinkovitch, Jemeppe-Sur-Sambre (BE); Philippe Gabant, Brussels (BE)

(73) Assignee: Universite Libre de Bruxelles, Brussels (BE)

( * ) Notice: Subject to any disclaimer, the term of this patent is extended or adjusted under 35 U.S.C. 154(b) by 1706 days.

(21) Appl. No.: 10/526,525

(22) PCT Filed: Sep. 3, 2003

(86) PCT No.: PCT/BE03/00147
§ 371 (c)(1),
(2), (4) Date: Aug. 26, 2005

(87) PCT Pub. No.: WO2004/022745
PCT Pub. Date: Mar. 18, 2004

(65) Prior Publication Data
US 2006/0088841 A1    Apr. 27, 2006

Related U.S. Application Data

(60) Provisional application No. 60/408,482, filed on Sep. 3, 2002.

(51) Int. Cl.
*C12N 15/74* (2006.01)
*C12N 15/00* (2006.01)
*C12N 15/02* (2006.01)
*C12N 1/21* (2006.01)
*C12N 1/00* (2006.01)

(52) U.S. Cl. ............... 435/480; 435/320.1; 435/325; 435/252.3; 435/254.11; 435/410

(58) Field of Classification Search ............ None
See application file for complete search history.

(56) References Cited

U.S. PATENT DOCUMENTS

| | | | |
|---|---|---|---|
| 5,300,431 | A | 4/1994 | Pierce et al. |
| 5,631,153 | A | 5/1997 | Capecchi et al. |
| 5,670,370 | A | 9/1997 | Molin et al. |
| 5,855,732 | A | 1/1999 | Yoshida |
| 5,888,732 | A | 3/1999 | Hartley et al. |
| 5,910,438 | A | 6/1999 | Bernard et al. |
| 5,922,583 | A | 7/1999 | Morsey |
| 6,143,557 | A | 11/2000 | Hartley et al. |
| 6,171,861 | B1 | 1/2001 | Hartley et al. |
| 6,180,407 | B1 | 1/2001 | Bernard et al. |
| 6,270,969 | B1 | 8/2001 | Hartley et al. |
| 6,271,359 | B1 | 8/2001 | Norris et al. |
| 2004/0115811 | A1 | 6/2004 | Gabant |
| 2005/0130308 | A1 | 6/2005 | Bernard |
| 2005/0260585 | A1 | 11/2005 | Szpirer |

FOREIGN PATENT DOCUMENTS

| | | |
|---|---|---|
| DE | 10038573 | 2/2002 |
| WO | WO 94/03616 | 2/1994 |
| WO | WO 97/14805 | 4/1997 |
| WO | WO 9713401 | 4/1997 |
| WO | WO 99/21977 | 5/1999 |
| WO | WO 99/58652 | 11/1999 |
| WO | WO 01/31039 | 5/2001 |
| WO | WO 01/42509 | 6/2001 |
| WO | WO 01/46444 | 6/2001 |
| WO | WO 02/12474 A2 | 2/2002 |
| WO | WO 02/066657 * | 8/2002 |

OTHER PUBLICATIONS

Pecota et al. (1997) Appl. Environ. Mocrobiol. 63:1917-1924.*
Herrero et al., J. Bacteriol., 172, 11, 6557-6567, 1990.*
Mori, Hirotada, et al. "Prophage λ Induction Caused by Mini-F Plasmid Genes." (1984) *Mol Gen Genet* 196:185-193.
(1992) Journal of Cellular Biochemistry, Keystone Symposia on Molecular & Cellular Biology, 104.
Abremski, et al. (1984) Bacteriophage P1 Site-specific Recombination. J. Bio. I. Chem. 259(3):1509-1514.
Aizenman, et al. (1996) An *Escherichia coli* chromosomal "addiction module" regulated by 3', 5'—bispyrophosphate: A modayk for programmed bacterial cell death. Proc. Natl. Acad. Sci. 93:6059-6063.
Backman, K. and H.W. Boyer (1983) "Tetracycline Resistance Determined by pBR322 is Mediated by one Polypeptide." Gene 26. pp. 197-203.
Bahassi, et al. (1995) F plasmid CcdB killer protein: *ccdB* gene mutants coding for non-cytotoxic proteins which retain their regulatory functions. Molecular Microbiology 15(6):1031-1037.
Baubonis, et al. (1993) Genomic Targeting with Purified Cre Recombinase. Nucleic Acids Research 21(9):2025-2029.
Baum, "Tn5401, a New Class II Transposable Element from *Bacillus thuringiensis*," Journal of Bacteriology, vol. 176. No. 10, May 1994, pp. 2835-2845.
Bech et al., "Seaqence of the reLB transcription unit from *Escherichia coli* and Identification of the reLB gene," The EMBO Journal, vol. 4, No. 4, pp. 1059-1066, 1985.
Bernard (1996) Positive Selection of Recombinant DNA by CcdB. BioTechniques 21(2)320-323. Bernard, et al. (1991) The 41 carboxy-terminal residues of the miniF plasmid CcdA protein are sufficient to antagonize the killer activity of the CcdB protein. Mol. Gen Genet 226:297-304.
Bernard, et al. (1992) Cell Killing by the F Plasmid CcdB protein involves poisoning of DNA-topoisomerase II complexes. J. Mol. Biol. 226:735-745.
Bernard, P., et al. (1994) Positive-Selection Vectors Using the F Plasmid ccdB Killer Gene. Gene 148, pp. 71-74.
Bex, et al. (1983) Mini-F encoded proteins: Identification of a new 10.5 kilodalton species. The EMBO Journal, 2(11):1853-1861.
Biswas, et al. (1993) High-Efficiency Gene Inactivation and Replacement System for Gram-Positive Bacteria. J. Bacteriology 175(11):3628-3635.
Bochner, et al. (1980) Positive Selection for Loss of Tetracycline Resistance. J. Bacteriology 143(2):923-933.
Boyd (1993) Turbo Cloning: A Fast, Efficient Method for Cloning PCR Products and Other Blunt-Ended DNA Fragments into Plasmids. Nucleic Acids Research 21(4):817-821.

(Continued)

*Primary Examiner* — Nancy T Vogel
(74) *Attorney, Agent, or Firm* — Knobbe, Martens, Olson & Bear LLP (57) ABSTRACT

The present invention is related to a reversible, parallel and/or multitask cloning method and kit, which improve the cloning of (preferably multiple) genetic element(s) in a nucleic acid construct such as vector or in chromosome of a cell and the rapid and efficient selection of said construct with a correct integration of said genetic element(s) either in vitro or in vivo.

31 Claims, 5 Drawing Sheets

OTHER PUBLICATIONS

Bravo, et al. (1988) Killing of *Escherichia coli* cells modulated by components of the stability system ParD of plasmid R1. Mol. Gen. Genet. 215:146-151.

Bubeck, et al. (1993) Rapid Cloning by Homologous Recombination in vivo. Nucleic Acids Research 21(15):3601-3602.

Bult, "Complete Genome Sequence of the Methanogenic Archaeon, Methanococcus Jannaschii," Science, vol. 273, Aug. 23, 1996, pp. 1058-1073.

Burns, et al. (1984) Positive Selection Vectors: A Small Plasmid Vector Useful for the Direct Selection of Sau2A-generated overlapping DNA Fragments. Gene 27:323-325.

Cole et al., "Deciphering the Biology of Mycobacterium Tuberculosis from the Complete Genome Sequence," Nature, vol. 393, Jun. 11, 1998, pp. 537-544.

Couturier, et al. (1998) Bacterial death by DNA gyrase poisoning. Trends in Microbiology 6(7):269-275.

Craine (1982) Novel Selection for Tetracycline-or Chloramphenicol—Sensitive *Escherichia coli*. J. Bacteriology 151(1):487-490.

Ebert et al. "A Moloney MLV-Rat Somatotropin Fusion Gene Produces Biologically Active Somatotropin in a transgenic pig." Molecular Endocrinology. 2:277-283, 1988.

Fleischmann et al., "Whole-Genome Random Sequencing and Assembly of *Haemophilus influenza* Rd," Science, vol. 269. pp. 496-512, Jul. 28, 1995.

Gabant et al., 1997 "Bifunctional lacZ a-ccdB Genes for selective Cloning of PCR Products," Biotechniques 23:938-941.

Gabant, P., et al. (1998) Direct Selection Cloning Vectors Adapted to the Genetic Analysis of Gram-Negative Bacteria and their Plasmids. Gene 207., pp. 87-92.

Gabant, P., et al. (2000) "New Positive Selection System Based on the parD (kis/kid)System of the R1 Plasmid." BioTechniques 28:784-788.

Gabant et al. 2001 "Use of Poison/antidote systems for selective Cloning," in Plasmid Biology 2000: International Symposium on Molecular Biology of Bacterial Plasmids, Meeting Abstracts, pp. 135-170, Plasmid 45:160-161.

Gerdes (2000) Toxin-Antitoxin modules may regulate synthesis of macromolecules during nutritional stress. Journal of Bacteriology 182:561-572.

Gossen, J.A., et al. (1992) Application of Galactose-Sensitive *E.coli* Strains as Selective Hosts for LacZ Plasmids. Nucleic Acids Res. 20,pp. 3254.

Gotfredsen, et al. (1998) The *Escherichia coli relBE* genes belong to a new toxin-antitoxin gene family. Molecular Microbiology 29(4):1065-1076.

Gronenborn (1978) Methylation of single-stranded DNA in vitro introduces new restriction endonuclease cleavage sites. Nature, 272:375-377.

Gronlund et al., "Toxin-Antitoxin Systems Homologous with relBE of *Escherichia coli* Plasmid P307 are Ubiquitous in Prokaryotes," Journal of Molecular Biology, vol. 285, No. 4, Jan. 29, 1999, pp. 1401-1415.

Guilfoyle, R.A., and L.M. Smith (1994) "A Direct Selection Strategy for Stotgun Cloning and Sequencing in the Bacteriophage M13." Nucleic Acids Res.22, pp. 100-107.

Guzman, L.M. et al. (1995) "Tight Regulation, Modulation and High-Level Expression by Vectors Containing the Arabinose Pbad Promoter." J. Bact. 177,pp. 4121-4130.

Hammer et al. "Genetic Engineering of Mammalian Embryos." J. Anim. Sci. 63:269-278, 1986.

Hartley et al. 2000 "DNA Cloning Using in Vitro Site-Specific Recombination," Genome Res. 10:1788-1795.

Hebsgaard, S.M., et al. (1996) "Splice Site Prediction in *Arabidopsis thaliana* Pre-mRNA by Combining Local and Global Sequence information." Nucleic Acids Research, 24(17) 3439-3452.

Henrich, et al. (1986) Use of the lysis gene of bateriophage φX174 for the construction of a positive selection of a positive selection vector. Gene 42:345-349.

Herrero, M., et al.(1990) "Transposon Vectors Containing Non-Antibiotic Resistance Selection markers for Cloning and Stable Chromosomal Insertion of Foreign Genes in Gram-Negative Bacteria." J. Bact. 172, pp. 6557-6567.

Holt, et al. (1993) A Novel Phage λ Replacement Cre-lox Vector that has Automatic Subcloning Capabilities. Gene 133:95-97.

Ioannou, et al. (1994) a new bacteriophage P1-derived vector for the propagation of large human DNA fragments. Nature Genetics 6:84-89.

Jensen, et al. 1995 "Comparison of ccd of F, parDE of RP4 , and parD of R1 using a novel conditional replication control system of plasmid R1," Mol. Microbiol. 17:211-220.

Jensen, R.B. and K. Gerdes (1995) "Programmed Cell Death in Bacteria: Proteic Plasmid Stabilization Systms." Mol. Microbiol. 17, pp. 205-210.

Kaneko et al., "Sequence Analysis of the Genome of the Unicellular Cyanobacterium *Synechocystis* sp. Strain PCC6803. II.Sequence Determination of the Entire Genome and Assignment of Potential Protein-Coding Regions," DNA Research, vol. 3, pp. 109-136. 1996.

Karoui, et al. (1983) *Ham22*, a mini-F mutation which is lethal to host cell and promotes recA-dependent induction of lambdoid prophage. The EMBO Journal. 2(11): 1863-1868.

Kuhn, et al (1986) Positive-selection vectors utilizing lethality of the EcoRI endonuclease. Gene,44:253-263.

Landy (1989) Dynamic, Structural, and Regulatory Aspects of λ Site-Specific Recombination. Annu. Rev. Biochem. 58:913-949.

Lehnherr, et al. (1993) Plasmid Addiction Genes of Bacteriophage P1: *doc*, which cause cell death on curing of prophage, and *phd*, which prevents host death when prophage is retained. J. Mol. Biol. 233:414-428.

Liu (1989) DNA Topoisomerase poisons as antitumor drugs. Annu. Rev. Biochem. 58:351-375.

Maki, et al (1992) Modulation of DNA Supercoiling Activity of *Escherichia coli* DNA Gyrase by F Plasmid. The Journal of Biological Chemistry vol. 267(17):12244-12251.

Maloy, et al. (1981) Selection for Loss of Tetracycline Resistance by *Escherichia coli*. J. Bacteriology 145(2):1110-1112.

Manning, P.A., "Nucleotide Sequence encoding the Mannose-fucose-resistant Hemagglutinin of Vibrio Cholerae 01 and Construction of a Mutant," EMBL Sequence Database, Aug. 7, 1993. pp. 1-7.

Maxwell, et al. (1986) Mechanistic aspects of DNA Topoisomerases. Advan. Protein Chem. 38:69-107.

Messing, et al. (1977) Filamentous coliphage M13 as a cloning vehicle: Insertion of a *Hind*II fragment of the *lac* regulatory region in M13 replicative form in vitro. Proc Natl. Acad. Sci. 74(9):3642-3646.

Miki, et al. (1984) Control of Cell Division by Sex Factor F in *Escherichia coli*. J. Mol. Biol. 174:605-625.

Miki, et al. (1984) Control of Cell Division by Sex Factor F in *Escherichia coli*. J. Mol. Biol. 174:627-646.

Moreadith et al. "Gene Targeting in Embryonic Stem Cells: The new Physiology and metabolism." J. Mol. Med. 75:208-216, 1997.

Mullins et al. "Perspective Series: Molecular Medicine in Genetically Engineered Animals." J. Clin. Invest. 98 (Suppl.): S37-S40, 1996.

Muyrers et al. 2001 "Techniques: rocombinogenic engineering—new options for cloning and manipulating DNA," Trends in Biochem. Sci. 26:325-331.

Murphy, et al. (1991) pλZd39:A New Type of cDNA Expression Vector for Low Background, High Efficiency Directional Cloning. Nucleic Acids Research 19(12):3403-3408.

Nilsson, et al. (1983) An Improved Positive Selection Plasmid Vector Constructed by Oligonucleotide Mediated Mutagenesis. Nucleic Acids Research 11(22):8019-8029.

Norrander, et al. (1983) Construction of improved M13 vectors using oligodeoxynucleotide-directed mutagenesis. Gene, 26:101-106.

Ogura, et al. (1983) Mini-F plasmid genes that couple host cell division to plasmid proliferation. Proc. Natl. Acad. Sci. USA, 80:4784-4788.

pGT-N28 Vector DNA (catalog #N3728) New England Biolabs Online Catalog, Jun. 2, 1999, p. 1, www.neb.com/neb/products/nucleic./307-28.html, the whole document.

pKO Scrambler Series Gene Targeting Vectors for Knockout Mice. Stratagene Online Catalog, Jan. 1998, pp. 1-3; www.stratagene.com/cellbio/toxicology/pko.htm, the whole document.

Peakman, et al. (1992) Highly Efficient Generation of Recombinant Baculoviruses by Enzymatically Mediated Site-Specific in vitro Recombination. Nucleic Acids Research 20(3):495-500.

Pecota et al. "Combining the Hok/Sok, parDE, and pnd Postsegregational killer loci to Enhance Plasmid Stability." Applied and Environmental Microbiology 63:1917-1924, 1997.

Pierce, et al. (1992) A positive selection vector for cloning high molecular weight DNA by the bacteriophage P1 system: Improved cloning efficacy. Proc. Natl. Acad. Sci. 89(6):2056-2060.

Roberts, et al. (1992) Definition of a Minimal Plasmid Stabilization System from the Broad-Host-Range Plasmid RK2. Journal of Bacteriology Dec. 1992:8119-8132.

Roberts, et al. (1994) The parDE operon of the broad-host-range plasmid RK2 specifies growth inhibition associated with plasmid loss. J. Mol. Biol. 18; 237 (1): 35-51.

Roca, et al. (1992) A Hit-and-Run System for Targeted Genetic Manipulations in Yeast. Nucleic Acid Research 20(17):4671-4672.

Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.

Ruiz-Echevarria, et al. (1991) Structural and functional comparison between the stability systems ParD of plasmid R1 and Ccd of plasmid. F. Mol. Gen. Genet 225:355-362.

Ruiz-Echevarria et al. 1995 "A Mutation that decreases the efficiency of Plasmid R1 Replication Leads to the Activation of parD, a Killer Stability System of the Plasmid," FEMS Microb. Letters 130:129-136.

Sadler, et al. (1980) Plasmids containing many tandem a synthetic lactose operator. Gene 8:279-300.

Salmon et al., "The Antidote and Autoregulatory Functions of the F Plasmid CcdA Protein: a Genetic and biochemical Survey" Molecular and General Genetics, vol. 244, pp. 530-538. 1994.

Sambrook, et al. (1989) Molecular Cloning: A Laboratory Manual. Cold Spring Harbor Laboratory Press, Cold Spring Harbor, NY, pp. xi-xxxviii.

Sambrook, et al. (1989) Molecular Cloning: A Laboratory Manual. Cold Spring Harbor Laboratory Press, Cold Spring Harbor, NY, pp. 4.12,A.9-A.13.

Saul, et al., "Nucleotide Sequence and Replication Characteristics of RepFIB, a Basic Replicon of IncF Plasmids," Journal of Bacteriology, vol. 171,No. 5, pp. 2697-2707, May 1989.

Schlieper et al. 1998 "A Positive Selection Vector for Cloning of Long Polymerase Chain Reaction Fragments based on a lethal mutant of the crp Gene of *Escherichia coli*," Anal. Biochem. 257:203-209.

Seamark, R.F. "Progress and Emerging Problems in Livestock Transgenesis: a Summary perspective." Repod. Fert. Dev. 6:653-657, 1994.

Smith, et al. (1985) Modification and Selection of Human Interleukin 2 Produced in Insect Cells by Baculovirus Expression Vector. Natl Acad. Sci. 82:8404-8408.

Smith, et al. (1997) The poison-antidote stability system of the broad-host-range *Thiobacilus ferroxidans* plasmid pTF-FC2. Molecular Microbiology 26(5):961-970.

Sierra et al. 1998 "Functional Interactions between chpB and parD, two homologous conditional killer systems found in the *Escherichia coli* chormosome and in plasmid R1," FEMS Microb. Letters 168:51-58.

Simons, R.W., et al. (1987) "Improved Single and Multicopy Lac-Based Cloning Vectors for Protein and Operon Fusions." Gene 53, pp. 85-96.

Tomb et al., "The Complete Genome Sequence of the Gastric Pathogen *Helicobacter pylori*," Nature. vol. 388, Aug. 7, 1997, pp. 539-547.

Tsuchimoto, et al. (1988) Two Genes, *pelK* and *peml*, responsible for stable maintenance of resistance plasmid R100. J. of Bateriol., 170(4):1461-1466.

Trudel, P., et al. (1996) pGATA: A Positive Selection Vector Based on the Toxicity of the Transcription Factor GATA-1 to Bacteria. BioTechniques. 20:684-693.

Tsuchimoto et al.,"The Stable Maintenance System pem of Plasmid R100: Degradation of Peml Protein May Allow PemK Protein to Inhibit Cell Growth." Journal of Bacteriology, vol. 174, No. 13, pp. 4205-4211, Jul. 1992.

Tsuchimoto, et al. (1993) Autoregulation by cooperative binding of the Peml and PemK proteins to the promoter region of the *pem* operon. 237:81-88.

Van Reeth, T., et al. (1998) "Positive Selection Vectors to Generate Fused Genes for the Expression of His-Tagged Proteins." *Biotechniques*. 25(5):898-904.

Vemet, T., et al. (1985) "A Direct-Selection Vector Derived from pColE3-CA38 and adapted for Foreign Gene Expression." Gene 34:87-93.

Wang (1985) DNA Topoisomerases. Ann. Rev. Biochem. 54:665-697.

Yanisch-Perron, et al. (1985) Improved M13 phage closing vectors and host strains: Nucleotide sequence of the M13mp18 and pUC19 vectors. Gen, 33:103-119.

Yarmolinsky (1995) Programmed cell death in bacterial populations. Science, 267:836-837.

Yu et al. 2000 "An Efficient recombination system for chromosome engineering in *Escherichia coli*," PNAS USA 97:5978-5983.

International Preliminary Examination Report from PCT/BE03/00045, dated Feb. 24, 2004.

International Preliminary Examination Report from PCT/BE02/00021, dated Feb. 19, 2003.

International Search Report from PCT/BE02/00021, Dated Jul. 12, 2002.

International Search Report from PCT/BE00/00151, Dated May 22, 2001.

Office Action from U.S. Appl. No. 09/634,039, Dated Dec. 16, 2004.
Office Action from U.S. Appl. No. 09/634,039, Dated Jun. 29, 2005.
Office Action from U.S. Appl. No. 09/634,039, Dated Dec. 20, 2001.
Notice of Allowability from U.S. Appl. No. 08/379,614, Dated Mar. 3, 1998.
Office Action from U.S. Appl. No. 09/225,152, dated Sep. 13, 1999.
Office Action from U.S. Appl. No. 08/379,614, Dated Aug. 27, 1996.
Office Action from U.S. Appl. No. 08/379,614, Dated Aug. 4, 1997.
Office Action from U.S. Appl. No. 09/634,039, Dated Jan. 15, 2003.
Office Action from U.S. Appl. No. 09/634,039, dated Sep. 24, 2003.
U.S. Appl. No. 09/634,039, filed Aug. 8, 2000.

* cited by examiner

REVERSIBLE, PARALLEL AND MULTITASK CLONING METHOD AND KIT

RELATED APPLICATIONS

This Application is the U.S. National Phase under 35 U.S.C. 371 of International Application No.: PCT/BE2003/000147, filed Sep. 3, 2003 designating the U.S. and published in English on Mar. 18, 2004 as WO 2004/022745, which claims the benefit of priority of U.S. Provisional Patent Application No. 60/408,482, filed Sep. 3, 2002, the entire disclosure of which is hereby expressly incorporated by reference.

FIELD OF THE INVENTION

The present invention is related to a reversible, parallel and/or multitask cloning method and kit, which improves the cloning of (preferably multiple) genetic element(s) in a nucleic acid construct such as a vector or the chromosome of a cell and the rapid and efficient selection of constructs with a correct integration of said genetic element (s), either in vitro or in vivo.

BACKGROUND OF THE INVENTION

To obtain complex molecular constructs comprised of multiple genetic elements, the selection of the genetic events (insertion(s) and/or deletion(s) and/or inversions(s) of DNA fragments) that will cause the assemblage of the target construct comprised of the said genetic elements at the right position and with the right orientation is usually a time consuming procedure.

In particular, one is necessary faced with the major problem of selecting different multiple genetic events (insertion, deletion, inversion of a genetic sequence in a nucleic acid construct), possibly in the same reaction tube.

Therefore, a molecular biologist should usually obtain a genetic event (insertion, deletion, inversion of a genetic sequence in a nucleic acid construct) separately and not simultaneously in the same reaction tube and should avoid any mistake (incorrect integration of a genetic sequence in the wrong direction, etc,) during said genetic manipulation.

AIMS OF THE INVENTION

A first aim of the invention concerns methods and tools which provide a solution to the above-mentioned problems, in particular methods and tools which allow a molecular biologist to insert and/or remove a genetic element, or to obtain a modification in the reading orientation of said genetic element (inversion) in a nucleotide sequence, either in vitro or in vivo.

Another aim of the present invention is to provide methods and tools which allow the creation of a genetic construct (such as a vector or the chromosome of a cell), either in vitro or in vivo, and assembled through the insertion(s), deletion(s) and/or inversion(s) of multiple genetic elements and the selection of the said genetic construct having incorporated (deleted or inverted) correctly these genetic elements.

A further aim of the present invention is to provide tools which allow a biologist to perform the step of the method in parallel and to perform at the same time multiple tasks (selection of multiple genetic events) in the same reaction tube or not.

A last aim of the present invention is to provide tools which allow that genetic events (insertions and deletions and inversions) are reversible, such that any nucleic acid construct can be viewed as a set of elements that can be recycled, i.e., re-used for the assemblage of other different nucleic acid constructs.

SUMMARY OF THE INVENTION

In the method and kit described hereafter, the person skilled in the art uses specific genetic constructs, which are the tools for performing the cloning and selection method according to the invention. Said tools are genetic constructs that could be integrated in vector(s) (plasmid(s) or virus(es), including bacteriophage(s)) or in the chromosomal genome of a cell suitable for obtaining the cloning and selection of the correct assemblage of various genetic elements. All these methods and systems allow the assemblage of one or more foreign genetic element(s) (target sequences of interest) in said nucleic acid construct vector or chromosome of a cell at specific sites. The integration of a foreign (preferably autologous) genetic element the nucleic acid construct of the invention could be done by techniques known to the person skilled in the art such as, but not limited to classical restriction/ligation, site specific recombination, TOPO cloning and homologous recombination. The assemblage of genetic elements can involve insertion(s), deletion(s) and/or inversion(s) of nucleotide sequences. In the method according to the invention, the selection of correctly inserted sequences is obtained by using specific markers, which are nucleotide sequences encoding molecules that are toxic for a cell or molecules which are inhibitors of such toxic molecules and/or block to toxic activity of such molecules expressed in the cell. Preferably, said molecules are either poison(s), and/or inhibitor(s) to poison(s), preferably selected from (but not restricted to) the group consisting of the following poison/antidote systems: Ccdb/Ccda, Kid/Kis, Hok/Sok, Doc/Phd, RelE/RelB, PasA/PasB/PasC, MazE/MazF, ParE/ParD.

In the method according to the invention, said foreign nucleotide elements are advantageously linked (at its 3' or 5' or both ends) to one or more promoter/operator nucleotide sequences, such as, but not limited to, constitutive promoters allowing the expression of a target nucleotide sequence incorporated in the nucleic acid construct according to the invention, when they are disposed according to the suitable and requested reading orientation.

In the method according to the invention, the person skilled in the art uses suitable cell strain(s) (prokaryotic and/or eukaryotic) which are either resistant or sensitive to one or more of said toxic molecules in order to obtain and select recombinant(s). The properties of cell strains can for example be due to the existence of gene(s) coding for poison and/or antidotes and integrated in the chromosome(s) of a cell or presented in episomal sequences such as plasmids.

Reversible Cloning and Selection Method and Kit

A first aspect of the present invention is related to a reversible cloning method and kit for which several specific preferred examples are described in details hereafter, in reference to the FIGS. 2 to 5.

Figure 3:
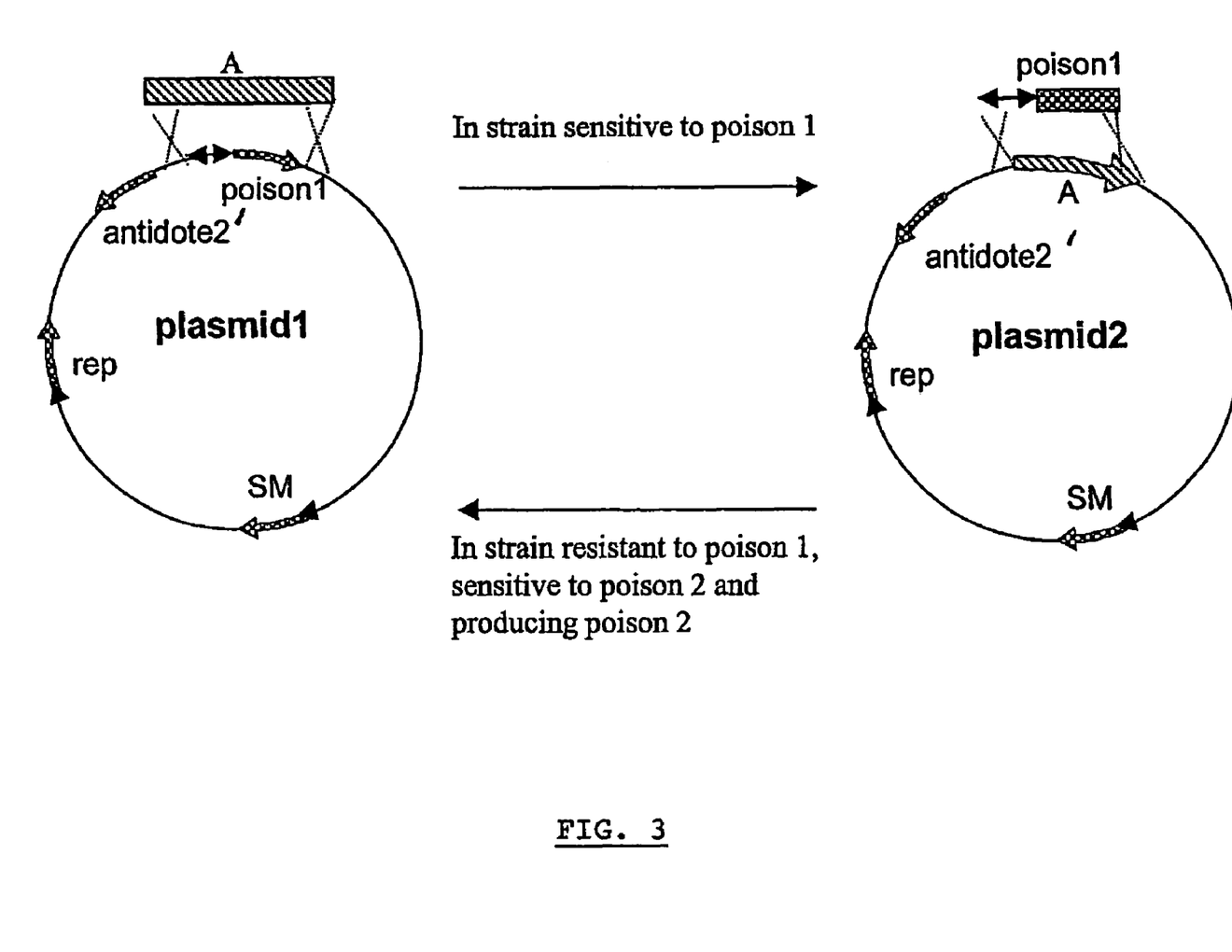
Figure 4:
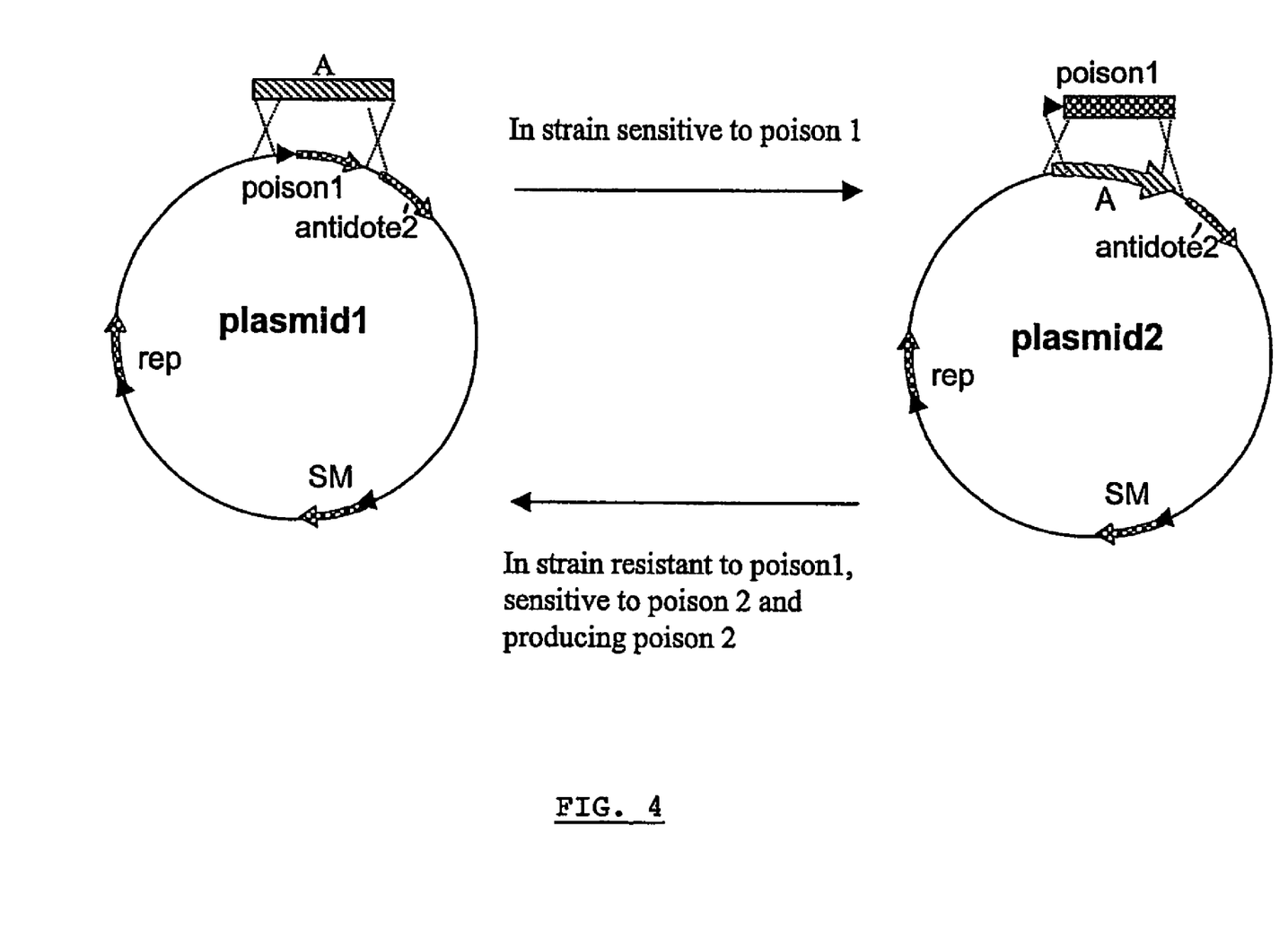

The elements used in the method of the invention are specific cells and a genetic preferably integrated in a vector or a chromosome of a cell comprised of either:

- a promoter/activator sequence 11 disposed upstream of a first and a second nucleotide sequence (1, 2) encoding two different toxic molecules (such as a poison 1 and a poison 2) (FIG. 2, left), or
- a first promoter/activator sequence 11 disposed upstream of a first nucleotide sequence 1 encoding a toxic molecule (such as a poison 1) and, disposed in the opposite reading direction of the first promoter/activator sequence 11, a second promoter/activator sequence 12 disposed upstream of a second nucleotide sequence encoding an antidote 2' to a second toxic molecule (such as poison 2) (FIG. 3, left), or a promoter/activator sequence 11 disposed upstream of a first and a second nucleotide sequence (1,2') encoding, respectively, a first toxic molecule (such as poison 1) and an antidote to a second toxic molecule (such as poison 2) different from said first toxic molecule (FIG. 4, left).

The terms "a nucleotide sequence encoding a toxic molecule or an antidote to a toxic molecule" also include sequences comprising multiple coding portions encoding several identical toxic molecules.

The insertion of a foreign target nucleotide sequence (A) "in" or as "a replacement" of the nucleotide sequence (1) encoding a toxic molecule element will allow either:

the inactivation of the nucleotide sequence 1 encoding the first toxic molecule, plus the activation or maintenance of the activation of the sequence 2 encoding the second toxic molecule (FIG. 2); or:

the inactivation of the first nucleotide sequence 1 encoding the first toxic molecule, plus the inactivation of the nucleotide sequence 2 encoding the antidote to the second toxic molecule (FIG. 3); or:

the inactivation of the first nucleotide sequence 1 encoding the first toxic molecule (FIG. 4).

The inserted foreign genetic element(s) (target sequence) may be a regulatory sequence or gene(s) of interest (possibly linked to one or more promoter/operator sequences).

Figure 2:
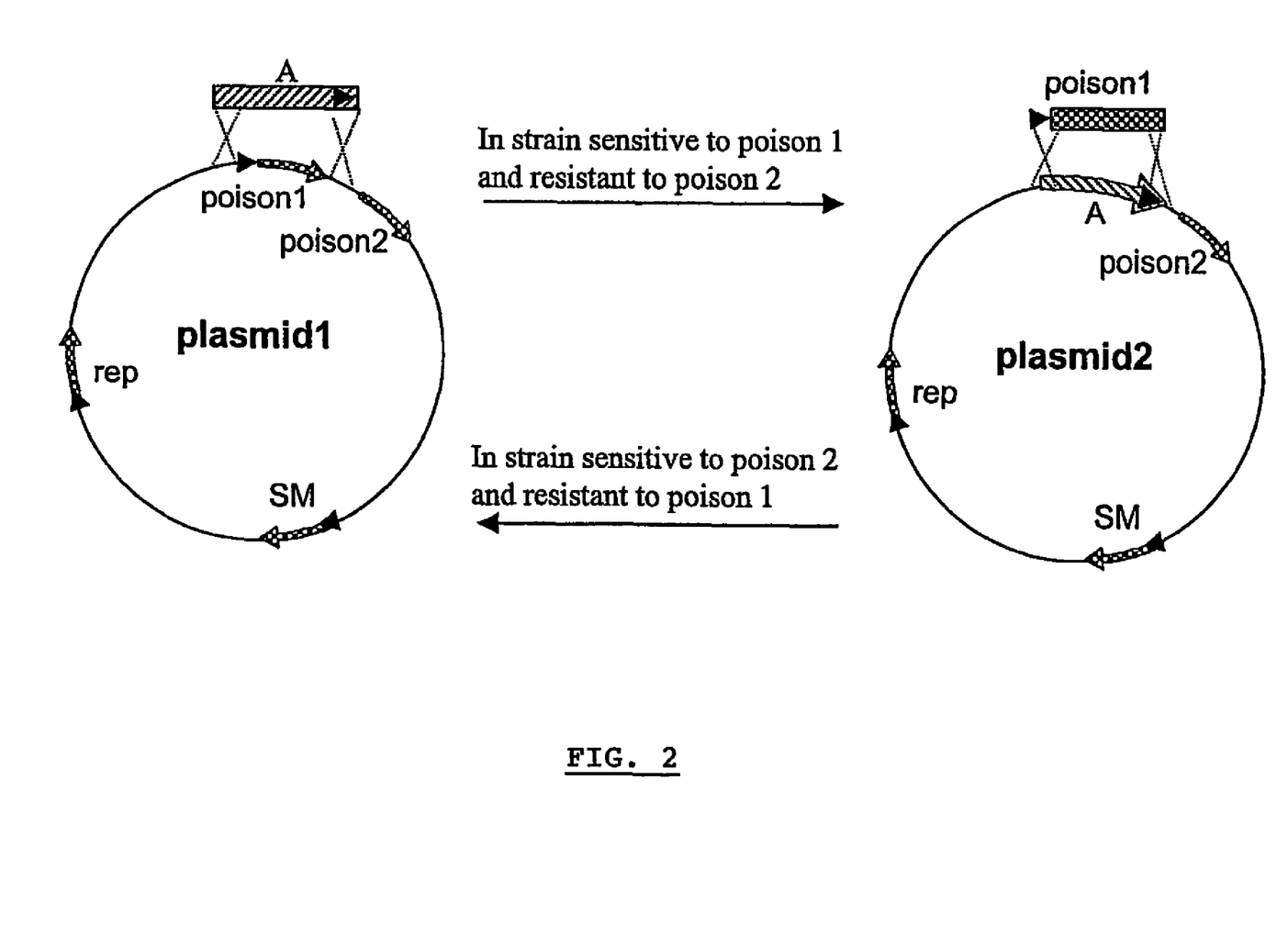

The selection of the genetic event (insertion) can be obtained in a cell strain sensitive to the first toxic molecule 1 (FIGS. 2&3&4) and possibly resistant to the second toxic molecule 2 (FIG. 2).

However, the said genetic event (insertion or replacement) is reversible through the replacement of the inserted element (target sequence) by the element that had been deleted following the recombination and insertion made in the first step. This reverse reaction deletion of a target sequence is selected in a strain both resistant to the toxic molecule 1 and sensitive to the toxic molecule 2 (FIGS. 2, 3, 4) plus, possibly, producing the toxic molecule 2 (FIGS. 3&4).

This reversible cloning and selection method is also suitable for obtaining an inversion of an integrated genetic element. A specific example is described in details hereafter, in reference to the FIG. 5. Indeed, the orientation of a sequence of interest can be reversed through the method of the invention (preferably following the insertion step of FIG. 4) or through a direct insertion of the target sequence between two different antidote sequences (1', 2'). Said genetic element (target sequence) associated to a promoter/operator (either at its 3' or 5' end), is initially integrated between two nucleotide sequences (1', 2') encoding respectively two different antidotes to two different toxic molecules 1 and 2. Said two nucleotide sequences (1', 2') encoding the two different antidotes are disposed in opposite reading orientations (disposed upstream and downstream the target nucleotide sequence in opposite divergent reading orientation). This construct allows to select for the recombination event(s) which will cause the target nucleotide sequence of interest and its associated promoter to have either the same orientation as the nucleotide sequence 1' encoding the first antidote to the first toxic molecule (selection done in a strain both sensitive to and producing poison 1) or the same orientation as the nucleotide sequence 2' encoding the second antidote to the second toxic molecule (selection done in a strain both sensitive to and producing poison 2). (see WO 02/066657 incorporated herein by reference)

Parallel and/or Multitask Cloning and Selection

Figure 1:
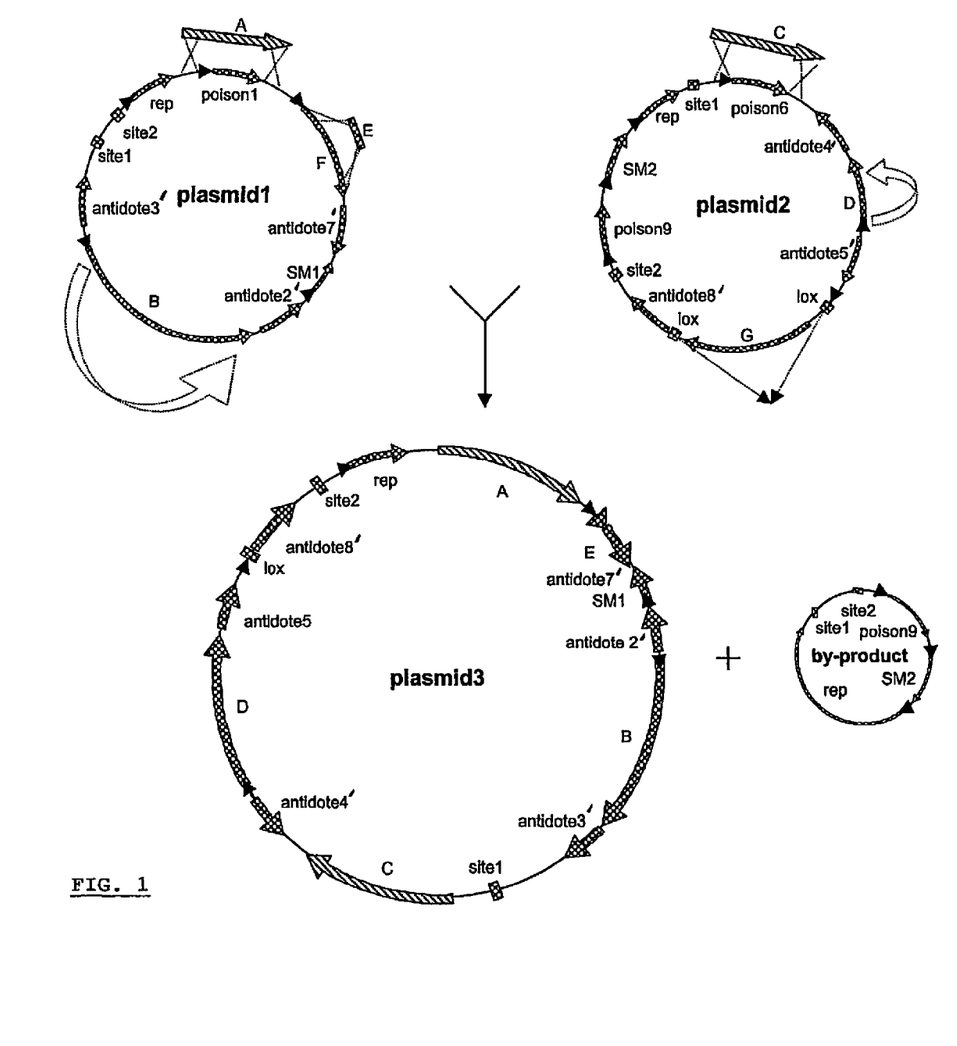

The above-mentioned reversible cloning and selection method and elements (nucleic acid construct or vector and specific cells strains) can also be used in a parallel and/or multitask cloning and selection method described hereafter (in details in the following example in reference to the FIG. 1).

The assemblage of multiple foreign genetic elements (different target sequences) in the vector or in the chromosome of a cell (either in vitro or in vivo) and the selection of the correct assemblage is obtained by the use of multiple nucleic acid construct comprising sequences encoding one or more (different or identical) toxic molecules and/or their antidotes. According to the type of the nucleic acid construct and the type of selective markers (encoding toxic molecules(s) and/or antidote(s) to toxic molecule(s)), the person skilled in the art can select the suitable events of insertion(s), deletion(s) and/or inversion(s) applied with said multiple genetic element(s).

Said cloning and selection method may require multiple steps possibly performed (sequentially) in the same reaction tube or inside a single cell.

Said method can be combined with the steps and means for performing in vitro protein synthesis (using in vitro transcription and translation kits).

Another aspect of the present invention is related to the algorithms, computer programs, and data bases (comprised of codes and means possibly stored in a computer readable medium) that can assist performing one or more step(s) of the method according to the invention. Said algorithms, data bases, and program codes means are used to define the correct combination of (but not limited to):

suitable markers (encoding the toxic molecule and/or the antidotes to said toxic molecule);

suitable cell strain(s) for selecting the suitable genetic events;

suitable pre-starting nucleic acid construct(s), suitable genetic element(s) (target nucleotide sequences and/or their operator/promoter sequences) to be inserted, deleted and/or reversed;

reaction mixture (including but not restricted to recombines mixtures, buffer, media, enzymes, . . . ) that are necessary for the assemblage/production of the molecular construct.

The algorithms, computer programs, and data bases are also able to control one or more step(s) of the method according to the invention, possibly performed by automate (s).

Another aspect of the present invention is related to kits of parts (cloning and/or selection kits) comprising the suitable elements for performing the method according to the invention, in particular computer programs mentioned above, nucleic acid construct(s), cell strain(s) and/or usual products and media used in the cloning and selection techniques.

Another aspect of the present invention is related to automates allowing to perform the method according to the invention and using the above-mentioned kit(s) of parts. Said kit(s) of parts (cloning and selection kits, combined with adequate media, cells and media present in vitro transcription and translation kits) and automates could also comprise other elements, such as a buffer solutions, pipeting element(s), primers for genetic amplification, cell culture media and means for recording results and for the storage of data.

The present invention will be described in detail in the following examples, in reference to the enclosed figures presented as non-limiting illustration of the various aspects of the present invention.

SHORT DESCRIPTION OF THE DRAWINGS

The FIG. 1 is an example of complex genetic construct obtained by parallel and multiple genetic events performed by the method of the present invention.

The FIGS. 2 to 5 are examples of reversible cloning and selecting method and kit according to the invention.

DETAILED DESCRIPTION OF THE INVENTION

This invention allows the making of complex genetic constructions through the use of (i) simultaneous and (ii) parallel events (the various recombinations and selection events present almost the same frequency). The "multitask" nature of the invention is defined as follows: for example, the invention allows to perform the insertion of genetic elements A and C, the deletion of genetic elements E and F, and the inversion of genetic elements B and D, some or all events (FIG. 1) being performed simultaneously in vitro (i.e., in the same tube) or in vivo (i.e., in the same organism). The final product of the above-mentioned events is a complex construct comprised of the genetic elements A, B, C, and D, all with the same orientation. The simultaneous selection of several genetic events (e.g., here, insertions, deletions, inversions, recombinations) is achieved through the use of a different selective marker (here poisons and antidotes genes for example) for each of the events. Filled black arrows represent promoters.

Plasmid 1 is amplified in a strain resistant to poison 1. Plasmid 2 is amplified in a strain resistant to poisons 6 and 9. Plasmid 3 is selected in a strain:
- sensitive to poisons 1 and 6 (for the selection of the insertion of genetic elements A and C),
- sensitive to poisons 3 and 5 (for the selection of the inversions of genetic elements B and D),
- sensitive to poisons 7 and 8 (for the selection of the deletions of genetic elements E and F),
- sensitive to poison 9 (for the selection of the recombination event between the construct made from plasmid 1 and the construct made from plasmid 2),
- and producing poison 3, poison 5, poison 7 and poison 8.

Realization of each "recombination" event can be done through techniques such as, but not limited to, classical restriction/ligation, site-specific recombination, or homologous recombination. Specificity of each genetic event (insertion, deletion, inversion, etc.) is insured by the specificity of the recombination event. For example, specificity of an insertion (both the location of the insertion and the orientation of the insert (target nucleotide sequence)) can be achieved by the use of different DNA sequences bordering both the insertion site and the fragment to be inserted (these DNA sequences can be selected by the man skilled in the art for performing said recombination event). These flanking sequences form either different site-specific recombination elements (in the case of site-specific recombination) or different elements of homology (in the case of homologous recombination). The simultaneous selection of several genetic events (e.g., an insertion, a deletion, and an inversion) is achieved through the use of a different selective marker for each of the events. As each of the genetic events is rare by nature, the selection for the simultaneous presence of all events requires the use of very efficient selective markers (e.g., but not limited to, antidote/poison genes).

The parallel cloning nature of the invention is defined as follows: N different genetic constructs that are produced in the same reaction mix (i.e., in the same tube) through the multitask process described above can be pre-designed such that their assemblage (here, the assemblage of the construct made from plasmid 1 with the construct made from plasmid 2) can be generated through recombination events as well. In other words, N−1 genetic constructs can be viewed as donors and 1 construct as a receptor. For example, N constructs can be combined through the use of n−1 selective markers for the selection of n−1 recombination events (FIG. 1).

Furthermore, the invention allows to use the products of the multitask/parallel cloning process as building blocks of new reactions. Indeed, a construct produced through the invention is a unique combination of building blocks that can be re-used for new (and different) constructs; i.e., the process is reversible and extendable, as shown in the FIGS. 2 to 4.

In FIG. 2, the DNA fragment to be inserted encodes for a target sequence of interest plus a promoter sequence located at its 3' end. The nucleic acid construct comprising the adequate insertion is selected by the deletion of the nucleotide sequence 1 encoding poison 1 in a strain sensitive to it but resistant to poison 2. The deletion of the target sequence (DNA fragment A) for re-use of the building block is achieved through the insertion of the DNA fragment initially removed (i.e., nucleotide sequence 1 encoding poison 1 with a promoter at its 5' end). This reverse event is selected in a strain sensitive to poison 2 and resistant to poison 1. Plasmid 1 is amplified in a strain resistant to poison 1. Plasmid 2 is amplified in a strain resistant to poison 2.

In FIG. 3, the insertion of the target sequence (DNA fragment A) is selected by the deletion of the nucleotide sequence 1 encoding poison 1 in a strain sensitive to it. The deletion of the DNA fragment A for re-use of the building block is achieved through the insertion of the DNA fragment initially removed (i.e., poison 1 with, at its 5' end, two promoters in opposite directions). This reverse event is selected in a strain allowing the conditional expression of poison 2, sensitive to poison 2, and resistant to poison 1. Plasmid 1 is amplified in a strain resistant to poison 1. Plasmid 2 is amplified in any strain whose viability is independent from the presence or absence of plasmid 2.

In FIG. 4, Plasmid 1 encodes both poison 1 and antidote 2 that are organized as an operon. The insertion of the target sequence (DNA fragment A) is selected by the deletion of the nucleotide sequence encoding poison 1 in a strain sensitive to it. The deletion of the target sequence (DNA fragment A) for re-use of the building block is achieved through the insertion of the DNA fragment initially removed (i.e., nucleotide sequence encoding poison 1 with a promoter at its 5' end). This reverse event is selected through the activation of the nucleotide sequence encoding antidote 2 in a strain allowing the conditional expression of poison 2, sensitive to poison 2, and resistant to poison 1. Plasmid 1 is amplified in a strain resistant to poison 1. Plasmid 2 is amplified in any strain whose viability is independent from the presence or absence of plasmid 2.

Figure 5:
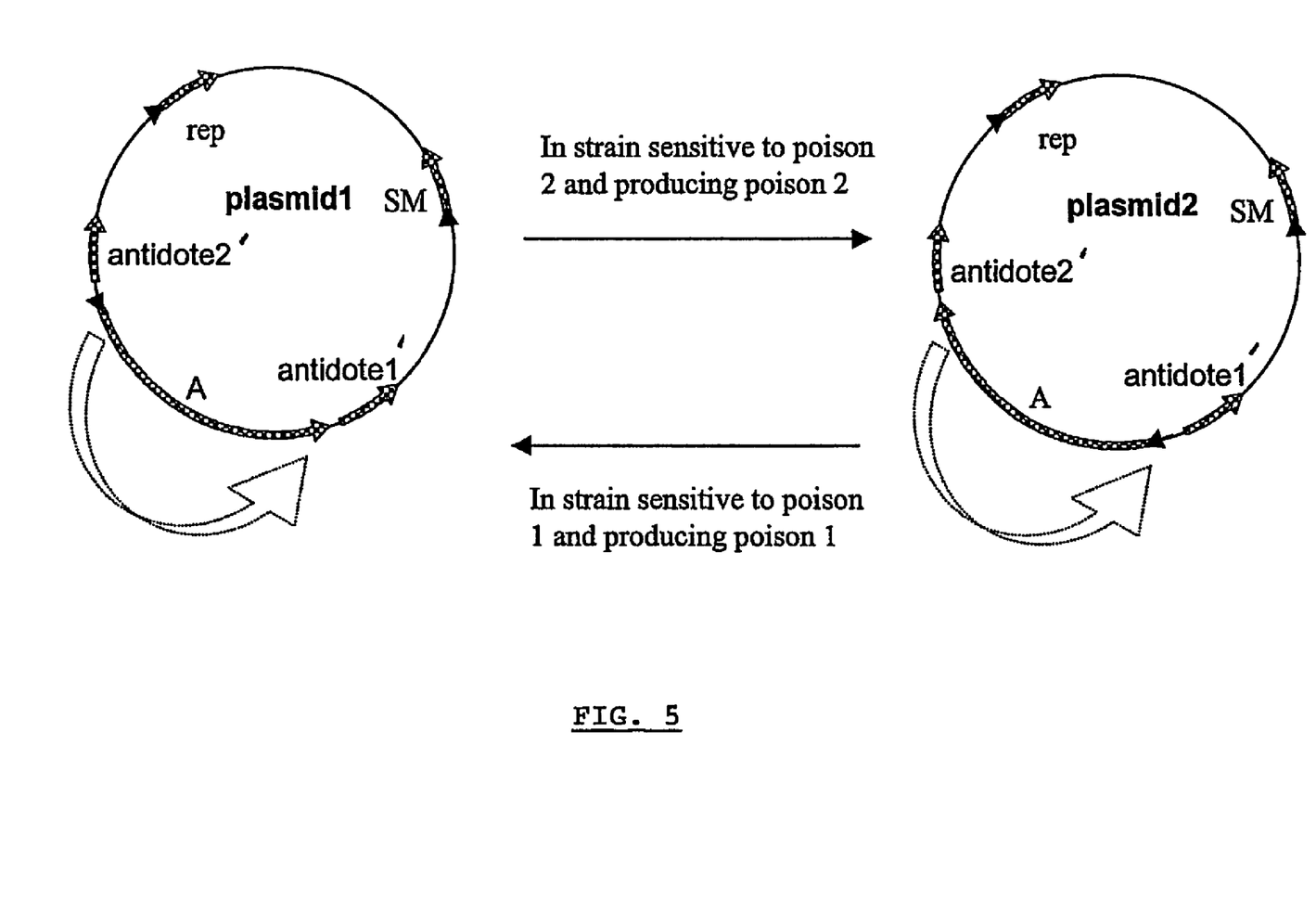

In FIG. 5, the target sequence (DNA fragment A) contains a promoter allowing the production of an antidote. The inversion of the DNA fragment A is selected using a strain allowing the conditional expression of poison 2 and sensitive to it. The reverse event is selected in a strain allowing the conditional expression of poison 1 and sensitive to it.

In other words, constructs produced through the invention are not dead-end products (i.e., useful for the only use they have been produced for); they can be recycled. This emphasizes the importance of the software component of the invention because it allows to create not only a data base of building blocks, but also of products that are followed up and stored (virtually in computers, and physically in freezers or other devices) for potential future uses. Because the software tracks the features of each building block and product, it also identifies those elements that are (i) necessary and (ii) intercompatible for future and new multitask/parallel/reversible processes.

The invention claimed is:
1. A recombinant genetic construct comprising:
   a) a vector comprising a first promoter/activator sequence disposed upstream of a first nucleotide sequence encoding a first poison protein, and a second promoter/activator sequence disposed upstream of a second nucleotide sequence encoding an antidote to a second poison protein different from said first poison protein, or b) a vector comprising a promoter/activator sequence disposed upstream of a first nucleotide sequence encoding a first poison protein and disposed upstream of a second nucleotide sequence encoding an antidote to a second poison protein different from said first poison protein,
  wherein the poison/antidote proteins are selected from the group consisting of CcdB/CcdA, Kid/Kis, Doc/Phd, RelE/RelB, PasA/PasB/PasC, MazE/MazF and ParE/ParD.

2. The genetic construct according to claim 1, wherein the genetic construct comprises:
  a first promoter/activator sequence disposed upstream of a first nucleotide sequence encoding a first poison protein and a second nucleotide sequence encoding an antidote to a second poison protein different from said first poison protein, wherein the second nucleotide sequence is disposed in an opposite direction to the reading orientation of the first promoter/activator sequence.

3. The genetic construct according to claim 2, wherein a third nucleotide sequence encoding an antidote to the first poison protein is under the control of a second promoter/activator sequence.

4. The genetic construct according to claim 1, wherein the genetic construct further comprises recombination sites disposed upstream and downstream the nucleotide sequence(s) encoding the first poison protein and the antidote to the second poison protein.

5. The genetic construct according to claim 1, wherein said vector further comprises an origin of replication and a selectable marker.

6. A cell transformed by the genetic construct according to claim 1.

7. The cell according to claim 6 which is selected from the group consisting of prokaryote cells, plant cells, animal cells and fungi cells.

8. A cloning and selection kit comprising at least one genetic construct according to claim 1 and cells to be transformed by said construct.

9. A selection method comprising the following steps:
  inserting a target nucleotide sequence into the genetic construct according to claim 1 such that the nucleotide sequence encoding the first poison protein cannot produce a functional poison protein; and
  selecting the genetic construct having integrated the target nucleotide sequence in a cell which is sensitive to said first poison protein.

10. The method according to claim 9 which further comprises the step of removing the inserted target nucleotide sequence thereby reconstituting the genetic construct.

11. The method according to claim 10, wherein said step of inserting the target nucleotide sequence is selected from the group consisting of restriction/ligation, site specific recombination, TOPO cloning and homologous recombination.

12. The method according to claim 9, wherein the inserting step comprises inserting a plurality of target nucleotide sequences.

13. The method according to claim 12, wherein the step of selecting the genetic construct comprising the plurality of target nucleotide sequences is made in a single cell or in a single reaction tube.

14. The genetic construct of claim 2, wherein said second nucleotide sequence encoding said antidote to said second poison protein is under the control of the second promoter/activator sequence.

15. The genetic construct of claim 5, wherein the selectable marker is an antibiotic resistance selectable marker.

16. The cell of claim 7, wherein said animal cells are human cells.

17. The cell of claim 7, wherein said fungi cells are yeast cells.

18. A recombinant genetic construct comprising a vector comprising a first promoter/activator sequence disposed upstream of a first nucleotide sequence encoding a first poison protein and a second promoter/activator sequence disposed upstream of a second nucleotide sequence encoding an antidote to a second poison protein different from said first poison protein,
  wherein the poison/antidote proteins are selected from the group consisting of CcdB/CcdA, Kid/Kis, Doc/Phd, RelE/RelB, PasA/PasB/PasC, MazE/MazF and ParE/ParD.

19. The genetic construct according to claim 18, wherein said first nucleotide sequence encoding a first poison protein is flanked by recombination sites.

20. The genetic construct according to claim 19, wherein said first promoter/activator sequence and said first nucleotide sequence encoding a first poison protein are together flanked by recombination sites.

21. The genetic construct according to claim 19, wherein an antibiotic resistance marker is not present between said recombination sites.

22. The genetic construct according to claim 18, wherein said first promoter/activator sequence is disposed in an opposite direction of said first nucleotide sequence.

23. A recombinant genetic construct comprising a vector comprising a promoter/activator sequence disposed upstream of a first nucleotide sequence encoding a first poison protein and disposed upstream of a second nucleotide sequence encoding an antidote to a second poison protein different from said first poison protein,
  wherein the poison/antidote proteins are selected from the group consisting of CcdB/CcdA, Kid/Kis, Doc/Phd, RelE/RelB, PasA/PasB/PasC, MazE/MazF and ParE/ParD.

24. The genetic construct according to claim 23, wherein said first nucleotide sequence encoding a first poison protein is flanked by recombination sites.

25. The genetic construct according to claim 24, promoter/activator sequence and said first nucleotide sequence encoding a first poison protein are together flanked by recombination sites.

26. The genetic construct according to claim 24, wherein an antibiotic resistance marker is not present between said recombination sites.

27. The genetic construct according to claim 4, wherein an antibiotic resistance marker is not present between said recombination sites.

28. The genetic construct according to claim 19, wherein said second nucleotide sequence is flanked by recombination sites.

29. The genetic construct according to claim 28, wherein an antibiotic resistance marker is not present between said recombination sites.

30. The genetic construct according to claim 24, wherein said second nucleotide sequence is flanked by recombination sites.

31. The genetic construct according to claim 30, wherein an antibiotic resistance marker is not present between said recombination sites.

* * * * *